(12) United States Patent
Quinn et al.

(10) Patent No.: US 7,767,463 B2
(45) Date of Patent: Aug. 3, 2010

(54) METHOD FOR SCREENING MOBILE PHASES IN CHROMATOGRAPHY SYSTEMS

(75) Inventors: Hubert M Quinn, Brighton, MA (US); Joseph J. Takarewski, Jr., Brookline, MA (US); Elizabeth Williams, Hopkinton, MA (US)

(73) Assignee: Cohesive Technologies, Inc., Franklin, MA (US)

( * ) Notice: Subject to any disclaimer, the term of this patent is extended or adjusted under 35 U.S.C. 154(b) by 305 days.

(21) Appl. No.: 11/763,983

(22) Filed: Jun. 15, 2007

(65) Prior Publication Data

US 2008/0307861 A1 Dec. 18, 2008

(51) Int. Cl.
*G01N 30/02* (2006.01)
*G01N 30/62* (2006.01)

(52) U.S. Cl. ............ 436/161; 73/54.01; 73/54.06; 73/61.47; 73/61.52; 73/61.58; 73/700

(58) Field of Classification Search ............ 436/161, 436/177, 178, 148
See application file for complete search history.

(56) References Cited

U.S. PATENT DOCUMENTS

| 4,924,716 | A | 5/1990 | Schneider |
| 6,004,822 | A | 12/1999 | Li et al. |
| 6,335,202 | B1 * | 1/2002 | Lee et al. ............ 436/161 |
| 6,788,409 | B2 | 9/2004 | Goodwin |
| 2005/0106745 | A1 | 5/2005 | Wexler et al. |
| 2005/0247625 | A1 * | 11/2005 | Liu et al. ............ 210/635 |
| 2007/0092404 | A1 | 4/2007 | Hughes |

FOREIGN PATENT DOCUMENTS

| EP | 0 448 837 A2 | 10/1991 |
| EP | 448837 A2 * | 10/1991 |

OTHER PUBLICATIONS

Krstulovic, A.M., Colin, H., Guiochon, G., Compariston of Methods Used for the Determination of Void Volume in Reversed-Phase Liquid Chromatography, 1982, Anal. Chem., 54, 2438-2443.*
Matsuura, T., 1994, CRC Press Inc., 1-72.*
Zou et al, Affinity Membrane Chromatography for the Analysis and Purification of Proteins, 2001, J. Biochem. Biophys. Methods, 49, 199-240.*

(Continued)

*Primary Examiner*—Vickie Kim
*Assistant Examiner*—Allison Gionta
(74) *Attorney, Agent, or Firm*—Grossman Tucker Perreault & Pfleger; Charles B. Katz

(57) ABSTRACT

A method and system of screening or selecting a mobile phase eluent for a chromatography column is provided. A sample for chromatographic analysis or purification is combined with a solvent and passed through a membrane. A pressure measurement is taken of the sample/solvent combination in the system prior to the membrane. The pressure measurement may be compared to a second pressure and an appropriate solvent may be selected based on the relationship between the first measured pressure and the second pressure.

12 Claims, 4 Drawing Sheets

OTHER PUBLICATIONS

Zhou et al., Membrane Supports as the Stationary Phase in High-Performance Immunoaffinity Chromatography, 1999, Anal. Chem., 71, 115-118.*

N.c. Van de Merbel, The use of ultrafiltration and column liquid chromatography for on-line fermentation monitoring, 1997, Trends in Analytical Chemistry, vol. 16, No. 3.*

W. Kiridena, C.F. Poole, Structure-driven retention model for solvent selection and optimization in reversed-phase thin-layer chromatography, 1998, Journal of Chromatography A, 335-347.*

Bartle et al., Measurement of Solubility in Supercritical Fluids Using Chromatographic Retention: the Solubility of Fluorene, Phenanthrene, and Pyrene in Carbon Dioxide, 1990, J. Chem. Eng., 35, 355-360.*

Thompson et al., High-Speed Liquid Chromatography by Simultaneous Optimization of Temperature and Eluent Composition, Anal. Chem., 2002, 74, 4150-4159.*

Cui et al., High-Performance Liquid Chromatography Using Mobile Phases with Enhanced Fluidity, 1991, Anal. Chem, 63, 1812-1819.*

D. Wexler et al., "Linking Solubility and Permeability Assays for Maximum Throughput and Reproducibility," Journal of Biomolecular Screening, vol. 10 (No. 4), pp. 383-390, (2005).

* cited by examiner

METHOD FOR SCREENING MOBILE PHASES IN CHROMATOGRAPHY SYSTEMS

FIELD OF THE INVENTION

The present invention relates to a method for screening mobile phase media as applied to a chromatographic system, such as a high performance liquid chromatography system (HPLC). The method provides, e.g., the ability to screen a given mobile phase for solubility, the ability to select a mobile phase for compound purification together with a procedure to advance more efficiently through a chromatographic purification process.

BACKGROUND OF THE INVENTION

U.S. Pat. No. 5,919,368, owned by the assignee herein, provides an excellent review regarding the utility of separations by high performance liquid chromatography. As noted therein, the separation process relies on the fact that a number of component solute molecules in a flowing stream of a fluid percolated through a packed bed of particles, known as the stationary phase, can be efficiently separated from one another. The individual components are separated because each component has a different affinity for the stationary phase, leading to a different rate of migration for each component and a different exit time for each component emerging from the column. The separation efficiency is determined by the amount of spreading of the solute band as it traverses the bed or column.

The '368 patent ultimately goes on to describe an improved method of performing liquid chromatography comprising the steps of packing within a tubular container a substantially uniformly distributed multiplicity of rigid, solid, porous particles with chromatographically active surfaces, so as to form a chromatographic column having an interstitial volume between said particles, said particles having average diameters of not less than 30 μm and loading said surfaces with at least one solute that is reactive with said surfaces, by flowing a liquid mixture containing said solute through said column at a velocity sufficient to induce flow of said mixture within at least a substantial portion of said interstitial volume at a reduced velocity greater than about 5000. The aforementioned method: 1. dramatically enhances both the speed and capacity of both analytical and preparative chromatography for both small and large molecules such as biologicals and the like; 2. is operative with mobile phase velocities considerably greater than any previously employed with significantly improved results; 3. makes use of packed particle beds in which the particles are substantially larger than those previously used in the art; and 4. offers a process that is operative at pressures considerably below those taught by the prior-art for turbulent flow chromatography. In that regard, attention is also directed to U.S. Pat. Nos. 5,772,874; 5,795,469; 5,968,367; 6,110,362 and 6,149,816, also owned by the assignee herein, which disclose other associated methods and apparatus for use in high performance chromatography applications, whose teachings are incorporated herein by reference.

Common to any HPLC method is the initial consideration of determining the solubility of the sample components for analysis/purification in a given mobile phase. The mobile phase refers to the solvent(s) that may be continuously applied to the column or stationary phase. The mobile phase therefore acts as a carrier for the sample solution. In, e.g. isocratic elution, component compounds may be eluted using a constant mobile phase composition. In gradient elution, different compounds may be eluted by increasing the strength of the organic solvent. In any event, screening or selection of a mobile phase composition and polarity may be vital for obtaining good separations. Proper selection of the mobile phase may therefore assist in preventing compounds from "crashing out" or precipitating out of the mobile phase during chromatographic analysis/purification.

SUMMARY OF THE INVENTION

An aspect of the present disclosure relates to a method of screening or selecting a mobile phase eluent for a chromatography column. The method may include combining a sample for chromatographic analysis or purification with a first selected mobile phase solvent. A membrane may be provided and a flow of the first mobile phase solvent containing the sample may be established through the membrane. A first pressure $P_1$ indicative of a resistance to the flow through the membrane may be measured and compared with a second pressure $P_2$. The mobile phase solvent may then be selected or rejected as an eluting solvent based upon a relationship between $P_1$ and $P_2$.

A further aspect of the present disclosure relates to a system for solubility screening of a mobile phase for chromatographic analysis/purification. The system may include a membrane and a membrane retention device, an input in fluid communication with the membrane and an output in fluid communication with the membrane. A pressure detector may be located between the input and the membrane.

BRIEF DESCRIPTION OF THE DRAWINGS

Features and advantages of the present invention will be apparent from the detailed description of embodiments below, which description should be considered in conjunction with the accompanying drawings, wherein.

DETAILED DESCRIPTION

Figure 1:
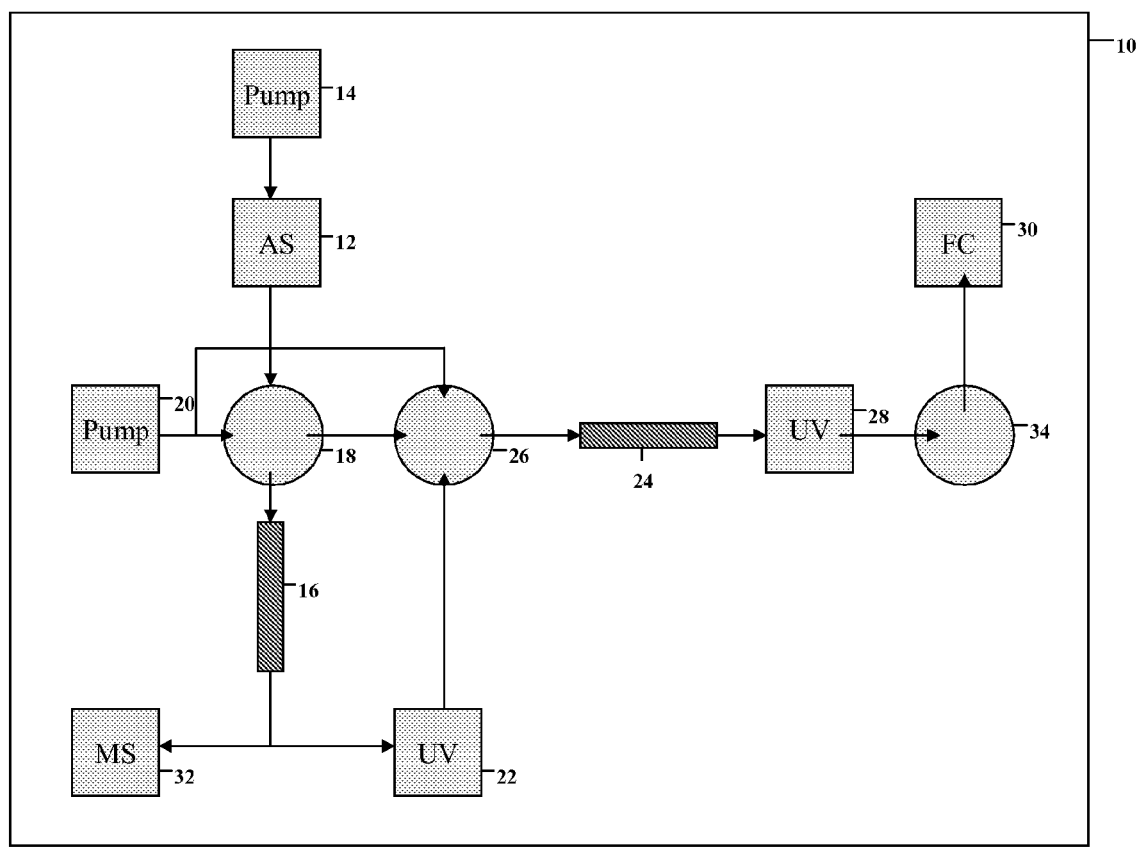
FIG. 1 illustrates in schematic view an exemplary liquid chromatography system.

An exemplary embodiment of a chromatography system 10 is shown in schematic view in FIG. 1. As shown in the schematic illustration, the system 10 may include an autosampler 12, containing at least one sample for chromatographic analysis/purification, and a first pump 14, such as an Agilent 1100 series model G1361A or G1312A, for providing means for loading a sample held by the autosampler 12. The system 10 may further include a first multi-port valve 18 for selectively passing a sample from the autosampler 12 to a first separation column 16. A second pump 20 may independently establish a flow of solvent, that is, a mobile phase component used to carry out dilution/mixing of the sample in the carrier mobile phase before entering the separation column 16 via the first multi-port valve 18. The system 10 may include a first detector 22 for identifying fractions/sample components of the effluent isolated or separated by column 16. Detector 22 may be a non-specific detector such as a UV detector and may be used in conjunction with a specific detector such as a Mass Spectrometer 32.

A second multi-port valve 26 may be provided for directing effluent from the first multi-port valve 18 or from the first detector 22 to a second recovery/concentration column 24. A sample component eluted from the second column 24 may be directed to a second detector 28. The system 10 may further include a third multiport valve 34 to direct eluent fraction(s) to a fraction collector 30 for receiving separated portions of the effluent exiting the second detector 28.

Both the first pump 14 and the second pump 20 may be high pressure binary pumps. As noted, the first pump 14 may be devoted to loading the column with a sample and the second pump 20 may be devoted to both loading and elution. As such, the first pump 14 may establish a flow of a loading solvent into the separation column 16 via the autosampler 12 and first valve 18. The second pump 20 may be adapted to provide a flow of an eluent having a variable strength. Providing a flow of eluent having variable strength may be accomplished, for example, by combining a primary eluent with a diluent, e.g., additional liquid components. Desirably the concentration of the eluent fluid in the mobile phase may be controlled either dynamically or according to a predetermined scheme.

The first separation column 16 and second column 24 may comprise a wide variety of columns suitable for use in the field of chromatography. For example, the columns 16, 24 may include high performance liquid chromatography (HPLC) columns, capillary electrophoresis columns, flow injection transfer lines, etc.

One particularly preferred variety of chromatography column herein, but by no means limiting, are those columns which include a substantially uniformly distributed multiplicity of rigid, solid, porous/pellicular particles with chromatographically active surfaces. The particles may have average diameters greater than about 30 μm, with the interstitial volume between the particles being not less than about 45% of the total volume of said column. The column may further include a means for loading the surface of the particles with at least one solute molecule that is reactive with the surfaces, by flowing a liquid mixture containing a loading solvent and the solute into said body, and flowing an eluent through said body at a velocity sufficient to induce flow of the eluent and solute within at least a substantial portion of the interstitial volume at a reduced velocity greater than about 5000.

The detectors 22, 28 and 32 may also include any of several varieties of detectors that are suitable for use with chromatography systems to detect the samples eluted through the columns. Suitable detectors for use with the system 10 herein may utilize identification systems including mass spectrometry, UV spectra, NMR, ELS (evaporative light scattering), refractive index, and fluorescence. The detector therefore provides identification/quantization of the desired component compounds of a sample by determining exactly when such a desired component compound is eluted from the exit end of the column. Those having skill in the art will appreciate that other similar systems for identifying eluted compounds may also be employed.

As a general overview of chromatographic analysis/purification, a sample may be dissolved in a given solvent and may be combined with a loading solvent capable of dissolving all of the compounds in the sample mixture. The solute sample may then be loaded on a chromatography column using the loading solvent as a transfer medium. The loading solvent may then be removed/depleted from the column, which can be accomplished by flushing with water or combinations thereof. The chromatography column may then be eluted with eluent fluids of increasing strength. Eluted fractions separated by the chromatography column may then be directed into a detector and characterized thereby. According to further embodiments, the separated fractions, or selected fractions, may be recovered.

As used in connection with any embodiment herein, the strength of an eluent is a relative measure of the ability of an eluent to elute a particular solute or compound from the stationary phase of a chromatography system. Generally, a stronger eluent may be suitable for use with sample components that are more strongly retained chromatographically, i.e., fraction that exhibit a strong affinity for, or interaction with, the stationary phase. However, compounds having a weaker affinity or interaction with the stationary phase, i.e., that are less chromatographically reactive, may be overwhelmed by a strong eluent resulting in inadequate separation of the compounds in a chromatography sample. The factors determining eluent strength may be related to the type of separation column employed and the chromatography technique utilized. In one embodiment, eluent strength may be a relative measure of the polarity of the fluid.

Incompatibility of any particular eluent with the solute or compound(s) for analysis/purification may prevent the elution of the solute or sample compound from the stationary phase of the chromatography system. The solute or compound(s) may "crash-out" or precipitate out of the eluent. The precipitation may result in an increase in pressure of the eluent as it passes through the stationary phase of the chromatography column. At this point, the analysis/purification is typically terminated, and the column is flushed with a cleaning solvent and the analysis/purification is then repeated with a different eluent selected to avoid precipitation. Such technique of trial and error to arrive at an appropriate eluent protocol typically is time-consuming and generally disruptive of the chromatography analysis/purification process.

Figure 2:
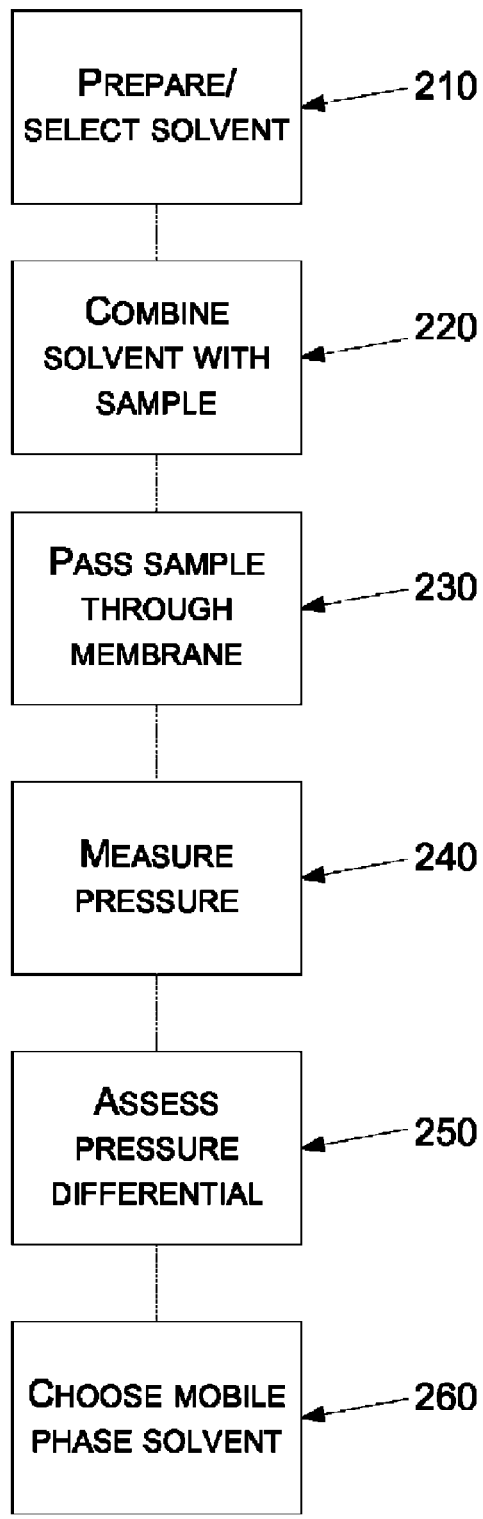
FIG. 2 illustrates an exemplary screening and selection method.

The method provided herein provides for a technique to more reliably screen and select an appropriate eluent protocol. In an exemplary embodiment, reference is therefore made to FIG. 2. A given solvent or solvent combination may be prepared 210. Then a desired sample, alone or premixed with the same or another solvent, may be combined with the given solvent forming a mobile phase 220. The mobile phase may then be passed through a membrane 230. As discussed more fully below, the membrane may be representative of a particular chromatographic column with respect to variables such as pore diameter. The pressure of the mobile phase as it passes through the membrane may then be measured by pressure detectors on one or both sides of the membrane 240. The pressure differential between mobile phases containing the desired sample and various solvents may be assessed at 250. An appropriate solvent may therefore be selected as an eluting solvent based upon a pressure differential between one or more mobile phase solvents or solvent combinations 260. The pressure differential is reference to a difference between a pressure for acceptable mobile phase and a mobile phase that is indicative of some level insolubility of the mobile phase with a given sample. For example, if the sample is completely insoluble in a given mobile phase there may be a relatively large pressure differential between a mobile phase containing no sample and the mobile phase loaded with a sample for analysis. Such relatively large pressure differential may therefore indicate that a different eluting mobile phase is necessary for chromatographic analysis/purification. In addition, it should be appreciated that the present disclosure is not limited to simply distinguishing between samples that are completely insoluble in a given mobile phase, and samples that are completely soluble. The present invention therefore extends to identifying mobile phase protocols that may provide sufficient solubility for chromatographic analysis, but not necessarily complete solubility.

The pressure differential may therefore be selected to amount to any value that is associated with a given column and which is demonstrated to provide acceptable analysis/purification results. As a guide, the pressure differential may be less than about 45 bar. This may then include pressure differentials of about 10 bar, 5 bar, etc. from a given baseline or standard solvent.

As alluded to above, the membrane may be selected so as to simulate in part a given length of the stationary phase of the chromatographic column. For example, the membrane may exhibit similar interstitial volume or mean pore diameter of the stationary phase of a given column. The interstitial volume may be understood as the sum of the intraparticle volume (volume within the pores of the particles) and interparticle volume (volume between the particles), in the packed column. In an exemplary embodiment, the void volume of the membrane may be within +/−10% of the interstitial volume for a given height of the stationary phase of a column. The membrane may also have a mean pore diameter or average pore diameter in the range of about 40 Å to 100 μm, including all values and increments therein, 60 Å, 80 Å, 120 Å, etc. It should be appreciated however, that the membrane need not be identical to an actual column but may merely provide a reference as to the compatibility of a given sample in a given solvent or solvent combination.

The membrane may be formed of a polymeric material, metal, glass or ceramic material. For example a polymeric membrane may include fabric, film or sheet. The membrane may also be a woven or a nonwoven material. In an exemplary embodiment, the membrane may be a mesh screen in the range of about 2 to 100 microns, including all values and increments therein, such as 10 microns, 20 microns, etc. In another exemplary embodiment, a nonwoven material including a spunbond or meltblown microfiber may be provided. The membrane or material in which the membrane is composed of may also be modified, such as by hydrophilic, hydrophobic or ion exchange modification.

Figure 3:
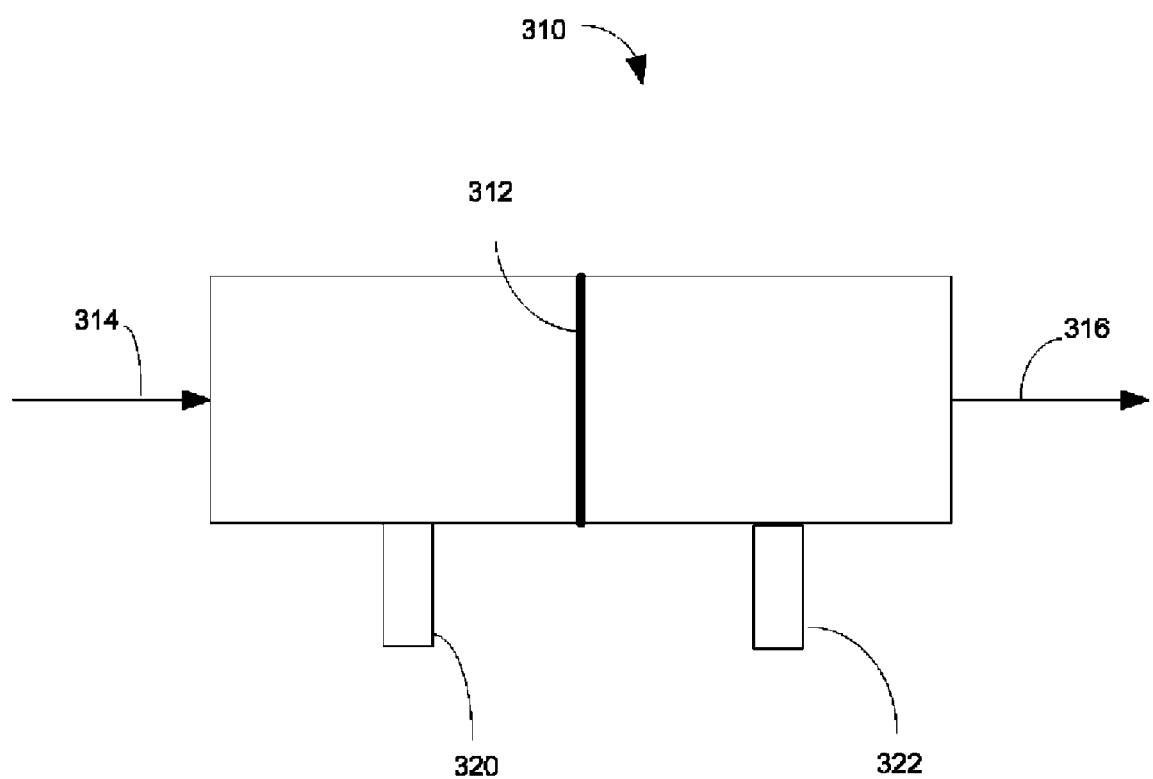
FIG. 3 illustrates an exemplary system for screening and selecting a mobile phase solvent(s).

In another aspect, a system is provided for passing a mobile phase through a membrane and measuring the pressure to pass the mobile phase through the membrane, as illustrated in FIG. 3. It may therefore be appreciated that the system in FIG. 3 may be integrated with the chromatographic system of FIG. 1. In this manner the system may be automated to screen/select a mobile phase for elution followed by chromatographic analysis. The membrane 312 may therefore be retained within a device 310, which includes an input 314 for the mobile phase to enter the device 310 and an output 316 for the mobile phase to exit the device. The membrane device may be a cartridge or other device or combination of elements that may retain the membrane. The cartridge may be inserted in a system of varying complexity. For example, a solvent reservoir may be provided to contain a given solvent. The solvent may be fed from the reservoir through the system by a pump. Optionally, a sample injector or injector valve may be provided to introduce the sample into the system. However, it should be understood that the sample may also be combined with the solvent in the solvent reservoir.

In an exemplary embodiment, the flow rate of the sample exiting the reservoir or injector may remain constant, while the flow rate through the membrane may vary. Stated another way, a given volume of the mobile phase may be introduced into the system over a given time interval. Once introduced into the system, the mobile phase may be passed into and through the membrane. The mobile phase may then be deposited into a collection or waste reservoir. In addition, a number of valves may be provided through out the system to allow for pressure relief, unidirectional flow or additional flow controls.

As alluded to above, a pressure detector such as a sensor, transducer or gauge (these terms are used interchangeably herein) may be located in the system prior to the membrane 320 and optionally, an additional pressure transducer may be located in the system after the membrane 322. The pressure detectors may be potentiometer, piezoelectric or other types of detectors known to those of ordinary skill in the art. The transducers may be mounted in a variety of locations and manners through out the system. In addition, the transducers may be mounted flush with the membrane device wall, substantially eliminating "dead volume" that may occur due to the presence of such devices within the system. Additionally, the pressure detector may communicate with a data acquisition system that may allow for the monitoring and/or recordation of the pressure as the mobile phase is introduced into and flows through the membrane.

The pressure developed prior to the membrane as the mobile phase passes through the membrane may be, as discussed above, indicative of the dissolution between the sample and the solvent. Accordingly, by comparing the pressure developed prior to the membrane of a given mobile phase $P_1$ with a sample to pressure developed by the same solvent without the sample, a pressure differential may be established that is indicative of sample solubility. In addition, by comparing the pressure developed prior to the membrane of a given mobile phase $P_1$ with a sample to a similar sample in other and different solvents, relative solubility may again be determined. Furthermore the pressure developed prior to the membrane of a given mobile phase $P_1$ with sample to another and different solvent without the sample $P_2$ may also provide information about relative sample solubility. Again, the pressure differential may be any value, but may be, e.g. a pressure differential of less than or equal to about 45 bar (i.e., $P_1-P_2 \leqq 45$ bar).

EXAMPLES

The following examples are for illustrative purposes only and are not meant to limit the scope of the disclosure described herein.

Figure 4:
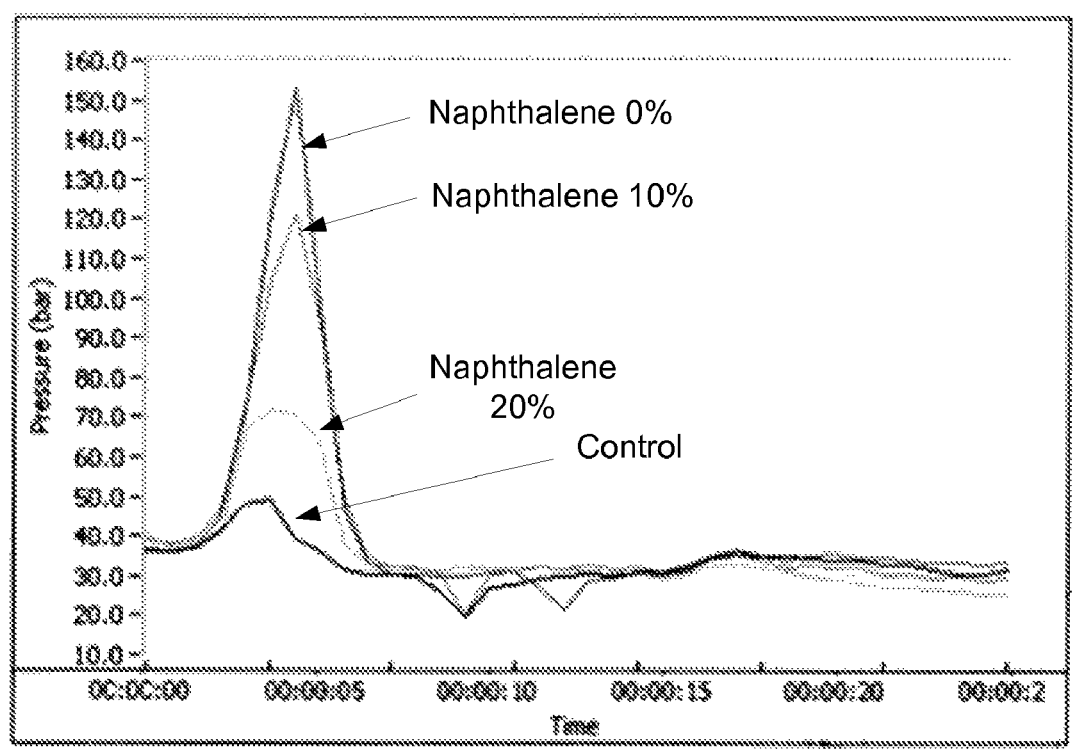
FIG. 4 illustrates exemplary pressure readings for a control solvent and a sample in three different mobile phase solvent combinations as measured by the methods and systems discloses herein.

Illustrated in FIG. 4 is the result of the pressure readings for a control solvent dimethyl sulfoxide (DMSO) and three (3) samples of naphthalene in $H_2O$, containing 0%, 10% and 20% of an organic solvent, i.e. acetonitrile. Five μL of each solvent/solvent combination was passed through the membrane and the pressure readings were taken prior to the membrane. As can be seen in FIG. 4, the control solvent exhibited a maximum pressure of approximately 45 bar. The naphthalene with 0% acetonitrile/100% water exhibited a maximum pressure of approximately 150 bar. Such a mobile phase (100% water) would clearly then be identified as unsuitable for chromatographic analysis for the column that is associated with the given membrane. The naphthalene with 10% acetonitrile/90% water exhibited a maximum pressure of approximately 120 bar. Once again, such a pressure may confirm that a 10% acetonitrile/90% water mixture as unsuitable as an appropriate mobile phase eluent. The naphthalene with 20% acetonitrile/80% water exhibited a maximum pressure of approximately 70 bar. When comparing such pressure of 70 bar to the pressure reading of 45 bar for the control solvent (DMSO), a pressure differential of 25 bar is identified which may then be utilized to select the 20% acetonitrile/80% water as an appropriate eluent.

Accordingly, pressure differentials between the control sample and the naphthalene samples were assessed, wherein the naphthalene was combined with different potential eluent protocols. The sample having the lowest pressure differential (20% acetonitrile/80% water) may then illustrate a desirable solvent combination for a given sample. It may also be observed that the naphthalene with 20% acetonitrile would be preferred over naphthalene with 0% and 10% acetonitrile.

The foregoing description is provided to illustrate and explain the present invention. However, the description hereinabove should not be considered to limit the scope of the invention set forth in the claims appended here to.

What is claimed is:

1. A method of screening a candidate solvent for use as an eluting solvent for chromatographic analysis, the method comprising:

combining a sample to be analyzed with the candidate solvent to form a first mobile phase;

providing a membrane and establishing a flow of said first mobile phase through said membrane;

measuring a first pressure $P_1$ at a location in the flow prior to the membrane indicative of a resistance to said flow through said membrane;

comparing said measured pressure $P_1$ against a second predetermined reference pressure $P_2$ to determine a pressure differential $P_1$-$P_2$;

selecting or rejecting said candidate solvent as an eluting solvent based upon the determined pressure differential $P_1$-$P_2$.

2. The method of claim 1 wherein the candidate solvent is selected as an eluting solvent if the determined pressure differential $P_1$-$P_2$ is less than or equal to 45 bar.

3. The method of claim 1 wherein said membrane has a void volume of greater than or equal to about 35%.

4. The method of claim 1 wherein said membrane has a mean pore diameter in the range of about 40 Å to 100 μm.

5. The method of claim 1 wherein said membrane is a mesh screen.

6. The method of claim 1 wherein said step of measuring pressure is performed by a pressure detector.

7. The method of claim 1 wherein said second predetermined reference pressure $P_2$ is determined by establishing a flow of the candidate solvent, absent addition of the sample, through said membrane, and measuring a pressure indicative of the resistance to flow through the membrane.

8. The method of claim 1 wherein said second pressure $P_2$ is determined by establishing a flow of a second solvent, different from the candidate solvent through said membrane, and measuring a pressure pressure indicative of the resistance to flow through the membrane.

9. The method of claim 1 wherein said flow is established by introducing a given volume of said mobile phase over a given time period.

10. The method of claim 1 wherein said membrane is a nonwoven material.

11. The method of claim 1 wherein said membrane is a ceramic material.

12. The method of claim 1 wherein said membrane is spunbond or meltblown.

* * * * *